United States Patent
Jensen et al.

(10) Patent No.: US 10,376,626 B2
(45) Date of Patent: Aug. 13, 2019

(54) DIALYZER HOLDER AND IMPROVED AIRLESS BLOODLINE PRIMING METHOD

(71) Applicant: Fresenius Medical Care Holdings, Inc., Waltham, MA (US)

(72) Inventors: Lynn E. Jensen, Syracuse, UT (US); DeLoy Lindley, Ogden, UT (US); Troy Dayton, Syracuse, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 568 days.

(21) Appl. No.: 14/774,414

(22) PCT Filed: Mar. 13, 2014

(86) PCT No.: PCT/US2014/025876
§ 371 (c)(1),
(2) Date: Sep. 10, 2015

(87) PCT Pub. No.: WO2014/151508
PCT Pub. Date: Sep. 25, 2014

(65) Prior Publication Data
US 2016/0022894 A1 Jan. 28, 2016

Related U.S. Application Data

(60) Provisional application No. 61/798,273, filed on Mar. 15, 2013.

(51) Int. Cl.
*A61G 7/05* (2006.01)
*A61M 1/16* (2006.01)
(Continued)

(52) U.S. Cl.
CPC ......... *A61M 1/1652* (2014.02); *A61G 7/0503* (2013.01); *A61M 1/3643* (2013.01);
(Continued)

(58) Field of Classification Search
CPC .............. B01D 61/30; B01D 2313/025; B01D 2313/06; A61M 1/16; A61M 1/1652; A61M 1/3643; A61M 1/3644; A61M 1/3649; A61M 2209/082; A61M 5/1415; A61M 2205/7536; A61M 1/288; A61M 1/3646; A61M 1/3647; A61M 1/365;
(Continued)

(56) References Cited

U.S. PATENT DOCUMENTS 2,540,584 A * 2/1951 Jaycox .................. A01K 97/10
224/922
4,211,380 A 7/1980 Lillegard et al.
(Continued)

FOREIGN PATENT DOCUMENTS

| EP | 0 747 074 A1 | 12/1996 |
| EP | 0830155 B1 | 3/1998 |
| WO | WO 2014/151508 A1 | 9/2014 |

OTHER PUBLICATIONS

Int'l Search Report for Int'l Application No. PCT/US2014/025876, titled: Improved Dialyzer Holder and Improved Airless Bloodline Priming Method, dated Jul. 29, 2014, 4 pages.

*Primary Examiner* — David C Mellon
(74) *Attorney, Agent, or Firm* — Hamilton, Brook, Smith & Reynolds, P.C.

(57) ABSTRACT

The present invention relates to a dialyzer holder to attach a dialyzer to a dialysis machine. During priming of a bloodline prior to a dialysis treatment, the dialyzer holder grips a dialyzer in approximately the center of the dialyzer, but allows movements of the dialyzer in an arc motion using two axes of rotation. The holder enables the dialyzer to move to a position where air can be primed from the dialyzer and, because the dialyzer can move toward the dialysis machine, this motion eliminates stress on the tubing connected to the bottom and top of the dialyzer and reduces the length of bloodline tubing necessary to accommodate dialyzer movement. The dialyzer holder incorporates an attachment point for a venous chamber for use during the priming procedure, enabling the venous chamber to move with the dialyzer, further reducing the tubing between the dialyzer and the venous chamber.

10 Claims, 10 Drawing Sheets

(51) Int. Cl.
*A61M 1/36* (2006.01)
*A61M 5/14* (2006.01)

(52) U.S. Cl.
CPC ........ *A61M 1/3644* (2014.02); *A61M 1/3649* (2014.02); *A61M 5/1415* (2013.01); *A61M 2205/7536* (2013.01); *A61M 2209/082* (2013.01)

(58) Field of Classification Search
CPC .......... A61M 1/3652; A61M 2209/084; A61B 50/20; A61G 7/0503
See application file for complete search history.

(56) References Cited

U.S. PATENT DOCUMENTS

| | | | | |
|---|---|---|---|---|
| 5,770,064 | A * | 6/1998 | Jonsson | A61M 1/16 210/232 |
| 6,409,131 | B1 * | 6/2002 | Bentley | A01K 97/10 248/219.4 |
| 7,138,053 | B2 * | 11/2006 | Sato | B01D 29/96 210/232 |
| 7,670,488 | B2 * | 3/2010 | Doyle | B01D 29/52 210/232 |
| 7,892,197 | B2 | 2/2011 | Folden et al. | |
| 8,123,947 | B2 | 2/2012 | Rohde et al. | |
| 2003/0135152 | A1 | 7/2003 | Kollar et al. | |
| 2008/0105605 | A1 * | 5/2008 | Kobayashi | B01D 61/18 210/209 |
| 2009/0101576 | A1 * | 4/2009 | Rohde | A61M 1/3643 210/646 |
| 2010/0126947 | A1 * | 5/2010 | Cole | B01D 35/30 210/791 |
| 2011/0168291 | A1 | 7/2011 | Beden et al. | |

\* cited by examiner

DIALYZER HOLDER AND IMPROVED AIRLESS BLOODLINE PRIMING METHOD

RELATED APPLICATIONS

This application is the U.S. National Stage of International Patent Application No. PCT/US2014/025876, filed Mar. 13, 2014, which designates the U.S., is published in English, and claims the benefit of and priority to U.S. provisional patent application Ser. No. 61/798,273, filed Mar. 15, 2013, the entirety of which is incorporated by reference herein.

BACKGROUND OF THE INVENTION

During set-up of a typical dialysis treatment, the blood side and dialysate side of the dialyzer are primed with saline. The dialyzer is typically rotated about its axis to invert the dialyzer. This is done to expel any air contained within the dialyzer blood compartment and dialysate compartment. This movement requires excess length of tubing that attaches the bloodline tubing to the dialyzer blood ports. Because this excess tubing length is only required during the priming procedure, it is excess tubing length and associated blood volume that is not required as part of the dialysis treatment.

SUMMARY OF THE INVENTION

The present invention provides for a dialyzer holder, which grips the dialyzer in approximately the center of the dialyzer, but allows movements of the dialyzer in an arc motion using two axes of rotation. This holder enables the dialyzer to move to a position where air can be primed from the dialyzer and, because the dialyzer moves toward the dialysis machine, this motion eliminates stress on the tubing connected to the bottom and top of the dialyzer, eliminating the need for longer bloodline tubing lengths to accommodate dialyzer movement. The dialyzer holder incorporates an attachment point for a venous chamber for use during the priming procedure, enabling the chamber to move with the dialyzer, further reducing the need to have excessive tubing between the dialyzer and the venous chamber.

Accordingly, example embodiments of the present invention relate to a holder for a dialyzer, having a blood side and a dialysate side both connected with tubing to a dialysis machine, configured to allow priming of the blood side and the dialysate side of the dialyzer without disconnecting the blood side or the dialysate side tubing from the dialysis machine. The holder has a dialyzer attachment member for securing the dialyzer in position and a rotational assembly connected to the attachment member, enabling it to rotate from an upright (e.g., vertical or substantially vertical) position used for priming the blood side of the dialyzer to a position more than 90 degrees from vertical for priming the dialysate side of the dialyzer. This holder enables the dialysate side of the dialyzer to be primed without disconnecting the blood side and it decreases the length of tubing necessary to retain the connection of the blood side of the dialyzer to the dialysis machine. Alternative embodiments can include enabling the dialyzer to rotate up to about 100 degrees from vertical. In other embodiments, the dialyzer holder includes an attachment member for securing the dialyzer holder to a support member.

In one embodiment, the dialyzer holder includes a venous chamber holder configured to attach a venous chamber about parallel to the dialyzer with the venous chamber fluidly connected to the blood side of the dialyzer. In some embodiments, the venous chamber includes an administration line having a hydrophobic vent adapted to remove gas from the blood side of the dialyzer.

In another embodiment, the length of the tubing that connects the blood side of the dialyzer to the dialysis machine is a minimized to allow the dialyzer to be rotated without disconnecting the blood side or dialysate side tubing from the dialysis machine.

In still another embodiment, the dialyzer holder's rotational assembly is configured to rotate the dialyzer about a rotational axis perpendicular to the long axis of the dialyzer. Alternative embodiments can include the rotational assembly configured to rotate the dialyzer counterclockwise. In a further embodiment, the dialyzer holder includes a second rotational assembly. The second rotational assembly can be configured to rotate the dialyzer about a second rotational axis perpendicular to the long axis of the dialyzer. Alternative embodiments can include the second rotational assembly configured to rotate the dialyzer counterclockwise.

In yet another example embodiment, a holder for a dialyzer, the dialyzer having a blood side and a dialysate side both connected with tubing to a dialysis machine, is configured to allow priming of the blood side and dialysate side of the dialyzer without disconnecting the blood side or dialysate side tubing from the dialysis machine. The holder has a dialyzer attachment member for securing the dialyzer in position, a first rotational member connected to the attachment member with a first rotational axis to allow the dialyzer to rotate from an upright (e.g., vertical or substantially vertical) position to a position about 45 degrees from substantially vertical, and a second rotational member connected to the attachment member with a second rotational axis allowing the dialyzer to rotate an additional about 55 degrees from the substantially vertical position to a position for priming the dialysate side of the dialyzer. Thus, this dual-axis configuration allows the dialysate side of the dialyzer to be primed without disconnecting the blood side while decreasing the length of tubing necessary to retain the connection of the blood side of the dialyzer to the dialysis machine.

Another example embodiment of the present invention relates to a method of priming a dialysis machine. The method includes connecting a blood line to a blood side, a dialysate line to a dialysate side, a pump loop, and a volume of saline to a dialyzer, priming the blood line with saline, rotating the dialyzer from an upright (e.g., vertical or substantially vertical) position for priming of the blood side of the dialyzer to a position more than 90° from the upright position for priming of the dialysate side of the dialyzer, thereby allowing priming of the dialysate side of the dialyzer without disconnecting the blood side while decreasing the length of tubing necessary to retain the connection of the blood side of the dialyzer to the dialysis machine, priming the dialysate side of the dialyzer with saline, and returning the dialyzer to an upright position, the dialyzer being held in a dialyzer holder including a dialyzer attachment member and a first rotational assembly connected to the attachment member.

In some embodiments of the method of priming a dialysis machine, the method further includes connecting a venous chamber to the blood line and attaching the venous chamber to the dialyzer by a venous chamber holder connected to the dialyzer attachment member prior to priming the blood line with saline. Rotating the dialyzer may include rotating up to about 100° from vertical.

In another embodiment, rotating the dialyzer includes rotating the dialyzer counterclockwise about the rotational axis. Rotating the dialyzer may include rotating about a second rotational assembly connected to the attachment member at a second connection, the second rotational assembly being configured to rotate the dialyzer about a second rotational axis perpendicular to the length of the dialyzer. In another embodiment, rotating the dialyzer about the second rotational assembly includes rotating the dialyzer counterclockwise about the second rotational axis.

In some embodiments, the method further includes removing gas from the blood line through an administration line having a hydrophobic vent on the administration line.

Compared to prior art dialyzers and corresponding methods of priming, the features of the present invention reduce the need for excess tubing. This reduces the risk of tangling the tubing when priming the dialysate side and generally when operating the dialysis machine. This feature also eliminates the need to disconnect the blood side of the dialyzer while priming the dialysate side.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

A dialyzer holder which grips the dialyzer in approximately the center of the dialyzer, but enables movement of the dialyzer in an arc motion is described herein. This holder enables the dialyzer to move to a position more than 90 degrees from vertical, where air can be evacuated from the dialyzer. Because the dialyzer moves toward the dialysis machine, this motion eliminates stress on the tubing connected to the bottom and top of the dialyzer, eliminating the need for longer bloodline tubing lengths to accommodate dialyzer movement. Additionally, shorter tubing lengths reduce the amount of blood outside of a patient's body during a dialysis treatment. The dialyzer holder includes a feature which temporarily holds the venous chamber during the priming procedure. Locating the venous chamber on the dialyzer holder enables the venous chamber to move with the dialyzer during priming.

In another aspect, a hydrophobic vent on the drug administration line of the venous chamber enables the drug administration line to automatically fill with saline during the priming procedure. The line is provided with a clamp that can be opened during the priming procedure or at the end of the priming procedure to automatically vent air from the venous chamber and the administration line. When the clamp is opened, the air is pushed up the administration line by saline within the chamber. When the air has completely exited the administration line, the saline contacts the hydrophobic cap blocking additional saline flow.

Figure 1:
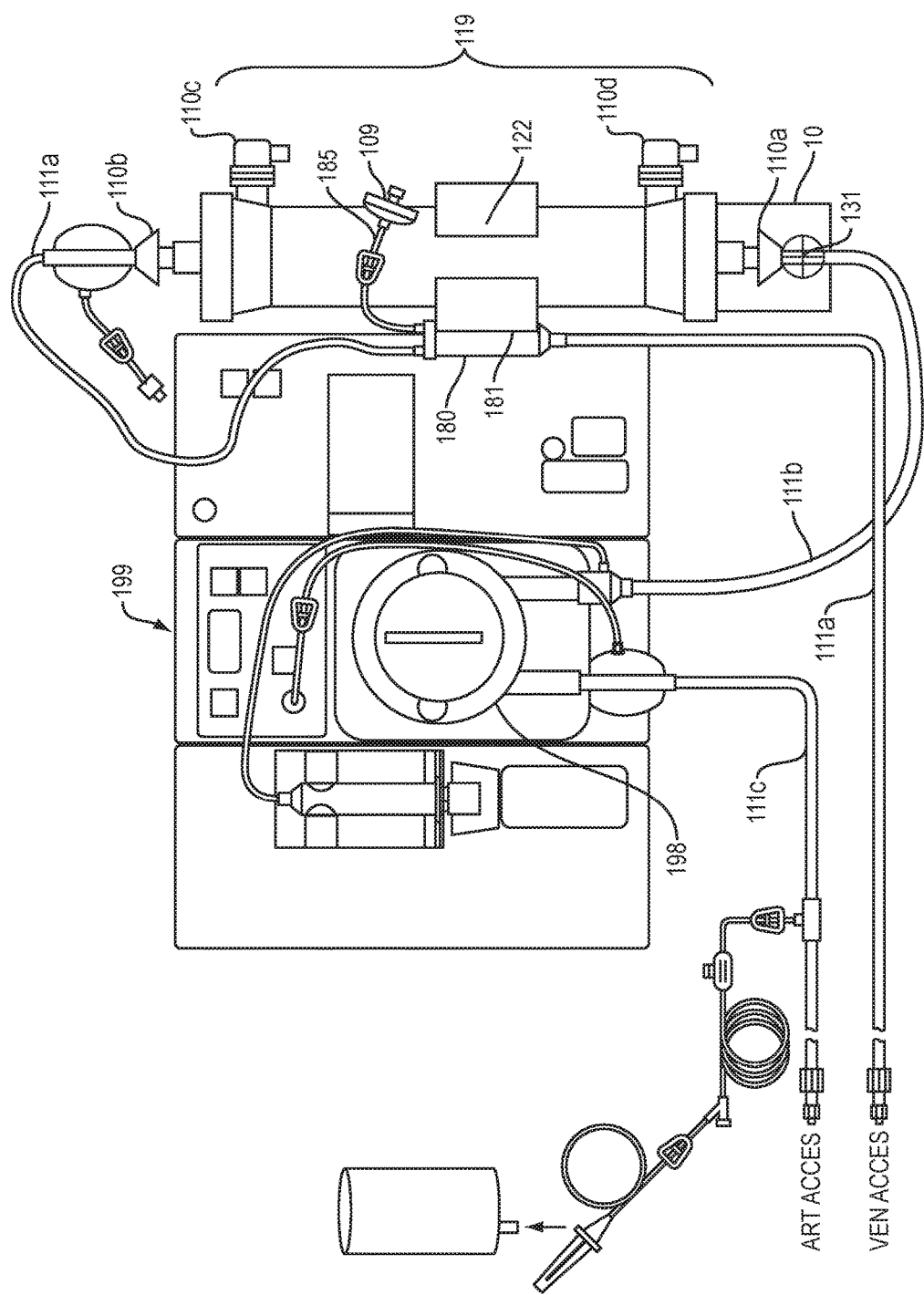
FIG. 1 is a diagram of a single axis dialyzer holder having elements of the present invention with an attached dialyzer connected to a dialysis machine.

FIG. 1 shows a single axis dialyzer holder 10 having elements of the present invention. A dialyzer 119 having a blood side and a dialysate side is connected to a dialysis machine 199 by blood tubing. Dialyzer 119 is shown in an upright (e.g., vertical or substantially vertical) position. Dialysis machine 199 includes a peristaltic pump 198 to draw blood from a patient via arterial access tubing 111c, pump it into the blood inlet side 110a of dialyzer 119 via blood supply tubing 111b, and back to the patient via venous access tubing 111a attached to the blood outlet side 110b of the dialyzer 119. Dialyzer holder 10 secures dialyzer 119 with clips 122 configured to snap around the profile of the long axis of the dialyzer 119. Dialyzer holder 10 has a rotation axis 131 enabling holder 10 and dialyzer 119 to rotate together about the rotation axis 131 for priming the dialysate side of dialyzer 119, when the dialysate outlet port 110d must be placed above the dialysate inlet port 110c to allow any trapped air to evacuate the dialysate side of the dialyzer 119. In operation, dialyzer 119 and dialyzer holder 10 rotates about rotation axis 131 until dialysate outlet port 110d is above dialysate inlet port 110c, as shown in FIG. 2.

Turning back to FIG. 1, dialyzer holder 10 additionally supports attachment of the venous chamber 180 by attaching the venous chamber to venous chamber holder 181 on dialyzer holder 10. A hydrophobic vent 109 attached to the venous chamber 180 via administration line 185 permits gases to escape from venous chamber 180. Additionally, administration line 185 can be configured to allow administration of a substance into the blood line.

Figure 2:
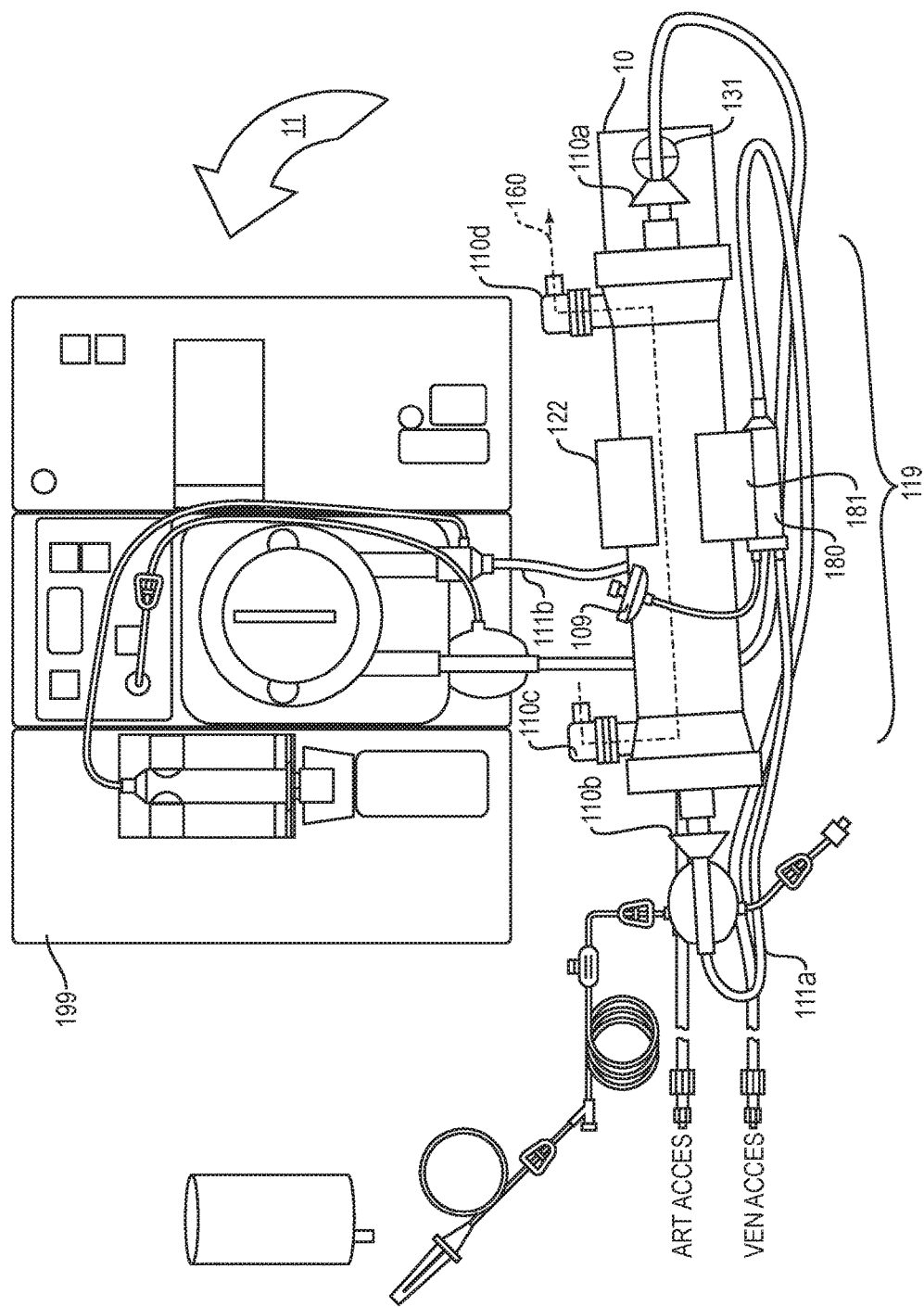
FIG. 2 is a diagram of the dialyzer holder of FIG. 1 positioned to prime the dialysate side of the attached dialyzer.

FIG. 2 shows dialysis machine 199 and dialyzer 119 system of FIG. 1 in a dialysate side priming configuration. A dialyzer 119 is secured by a set of clips 122 on a dialyzer holder 10. Clips 122 surround and grasp a portion of the circumference of the dialyzer to secure dialyzer 119 in the rotated position. Together dialyzer 119 and holder 10 are rotated counterclockwise 11 around axis 131, towards the dialysis machine 199, by more than 90 degrees off vertical. As shown in FIG. 2, dialysate outlet 110d of the dialysate side of dialyzer 199 is positioned above dialysate inlet side 110c and a volume of saline, sufficient to prime the dialysate side, is able to evacuate air 160 from the dialysate side of the dialyzer 119. A venous chamber holder 181 attached to the dialyzer holder 10 rotates the venous chamber 180 with dialyzer 119.

Figure 3:
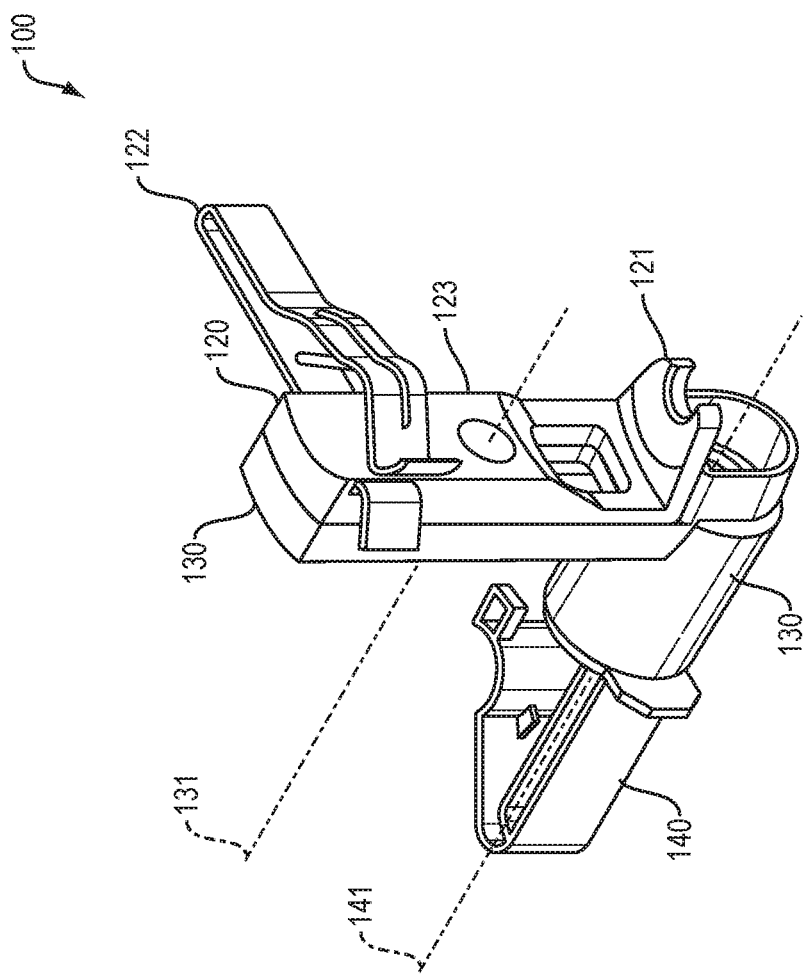
FIG. 3 is a diagram of a dual-axis dialyzer holder.

FIG. 3 is a diagram of a dual-axis dialyzer holder 100. Dual-axis dialyzer holder 100 has a dialyzer attachment member 120 configured to secure a dialyzer (119 in FIG. 6A) to a support member (151 in FIG. 6A) by support attachment member 140. As shown, support attachment member 140 can clip onto a cylindrical support pole via a support clip (150 in in FIG. 4), or to a dialysis machine (199 in FIG. 1), or another support member. In operation, dialyzer attachment member 120 secures a dialyzer (119 in FIG. 6A)

against curved face 123 with flex clip 122 applying pressure on a dialyzer (not shown) towards curved face 123 of dialyzer attachment member 120. Additionally, when a dialyzer is secured by flex clip 122, it is positioned along the curved dialyzer attachment member face 123 by dialyzer support member 121 configured to interface with an end of an attached dialyzer (not shown). As shown in FIG. 3, dialyzer attachment member 120 is able to rotate in one or both directions (clockwise and counterclockwise) about a second rotation axis 131 by being rotatably coupled to a rotation member 130. Likewise, the rotation member 130 is rotatably coupled to the support attachment members 140. Together, dialyzer attachment member 120 and rotation member 130 are able to rotate about support attachment member 140 at a first rotation axis 141.

Figure 4:
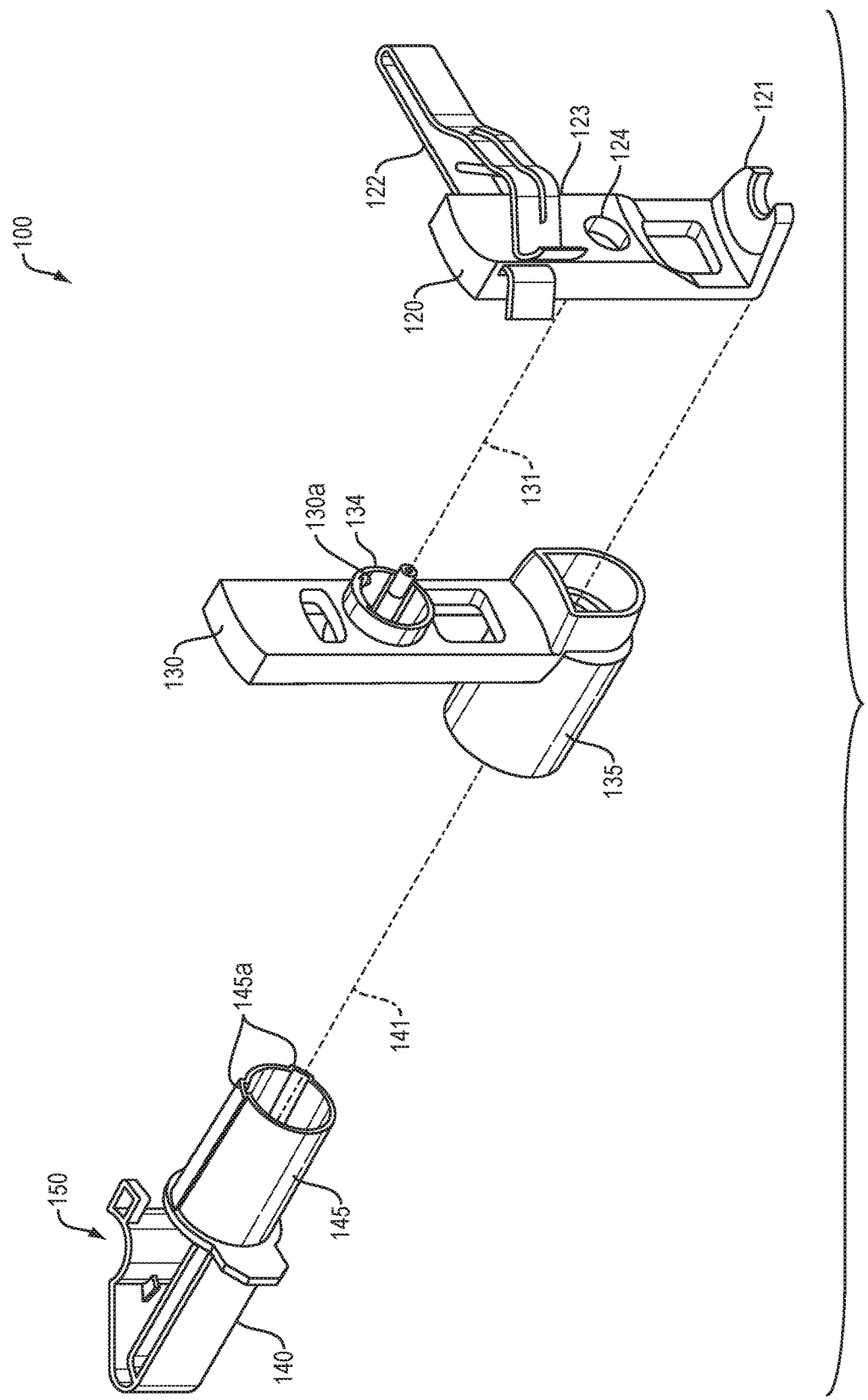
FIG. 4 is an exploded view of the dual-axis dialyzer holder of FIG. 3.

FIG. 4 is an exploded view of the dual-axis dialyzer holder of FIG. 3, showing dialyzer support member 140, rotation member 130, and dialyzer attachment member 120 separated along their respective rotation axes 131, 141. Dual-axis dialyzer holder 100 has dialyzer attachment member 120 configured to secure a dialyzer (119 in FIG. 6A) to a support member (151 in FIG. 6A) by support attachment member 140. As shown, support attachment member 140 can clip onto a cylindrical support pole via support clip 150. In operation, dialyzer attachment member 120 secures a dialyzer (119 FIG. 6A) against curved face 123 with flex clip 122 configured to apply pressure on the dialyzer (not shown in FIG. 4) towards curved face 123 of dialyzer attachment member 120. Additionally, an attached dialyzer (not shown in FIG. 4) is positioned along curved dialyzer attachment member face 123 by dialyzer support member 121 configured to interface with an end of an attached dialyzer (not shown in FIG. 4).

Continuing to refer to FIG. 4, rotation member 130 is rotatably coupled to support attachment members 140 and rotates about first axis 141. The rotation member 130 further includes first female rotation interface 135 configured to attach dialyzer support member 140 via corresponding first male rotation interface 145 on dialyzer support member 140. Likewise, dialyzer attachment member 120 is rotatably coupled to rotation member 130 and rotates about second axis 131. The rotation member 130 includes second male rotation interface 134 configured to attach dialyzer attachment member 120 via corresponding second female rotation interface 124 on dialyzer attachment member 120. Together, dialyzer attachment member 120 and rotation member 130 are able to rotate about support attachment member 140 at first axis 141.

Figure 5:
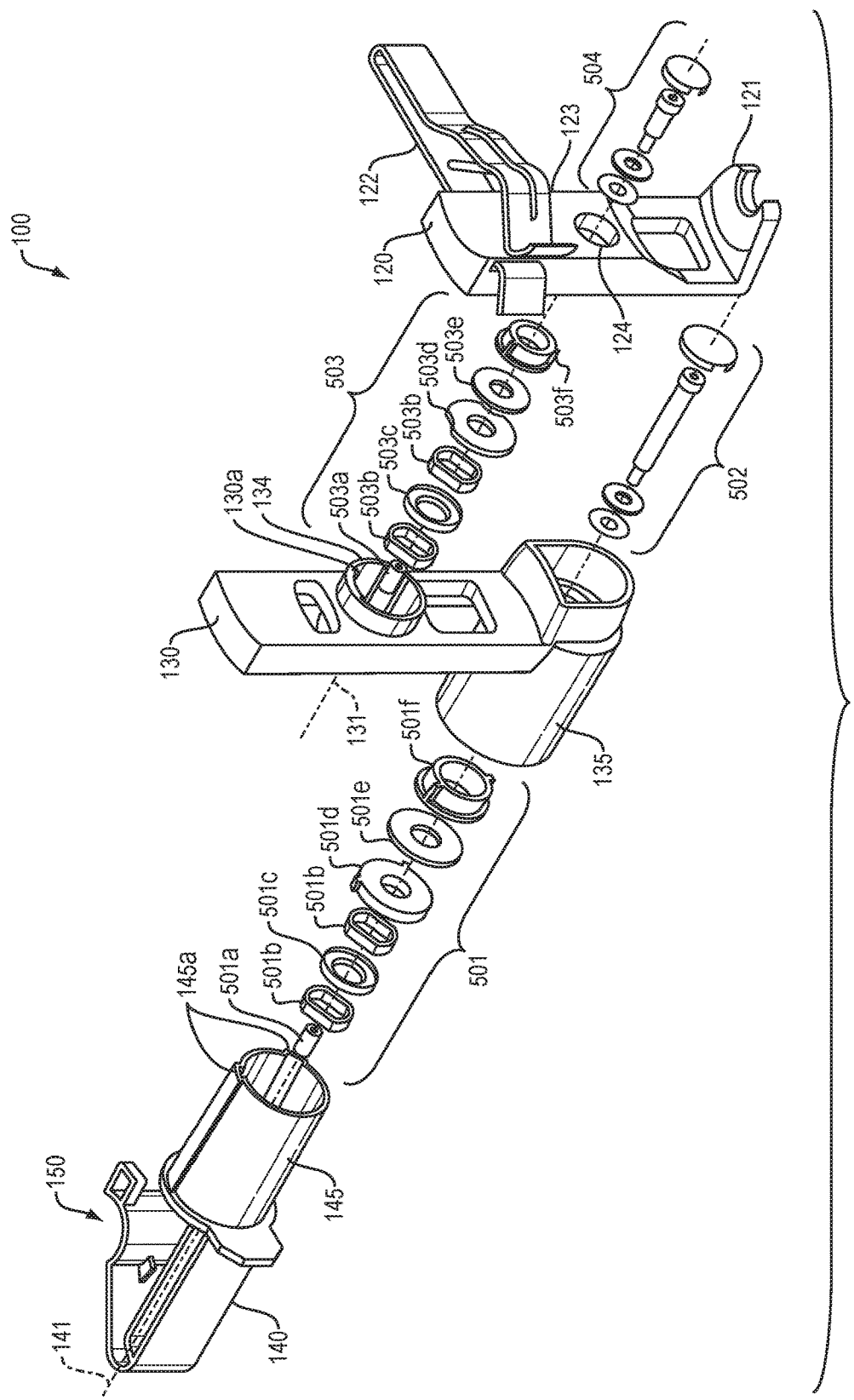
FIG. 5 is a further exploded view of the dual-axis dialyzer holder of FIG. 3, showing internal elements.

FIG. 5 is a further exploded view of the dual-axis dialyzer holder of FIG. 3, showing internal elements 501, 502, 503, 504 that enable rotation about the first and second rotation axes. First outer coupling assembly 501 is positioned between first female rotation interface 135 of rotation member 130 and corresponding first male rotation interface 145 on dialyzer support member 140. First outer coupling assembly 501 can include washers and bearing necessary to permit rotation of rotation member 130 with a dialyzer (not shown) attached to dialyzer attachment member 120. First outer coupling assembly 501 includes threaded insert 501a, wave springs 501b, spring spacer 501c, keyed washer 501d, washer 501e, and keyed washer 501f. First male rotation interface 145 can include one or more limit mechanisms (protrusion 145a) to limit the available angular rotation of rotation member 130 and first outer coupling assembly 501 can include tension or resistance mechanism (501a, 501b, 501c, 501d, 501e, and 501f) to enable dialyzer holder 100 to securely hold a dialyzer (not shown) attached to dialyzer attachment member 120 at arbitrary angles. First inner coupling assembly 502 is configured to fit inside first outer coupling assembly 501 and secures rotation member 130 to dialyzer support member 140 along a first axis 141. First inner coupling assembly 502 can include a screw and corresponding washers to fasten rotation member 130 to a corresponding screw hole in first male rotation interface 145 of dialyzer support member 140.

Second outer coupling assembly 503 is positioned between second female rotation interface 134 of rotation member 130 and second male rotation interface 124 on dialyzer attachment member 120. Second outer coupling assembly 503 can include washers and bearing necessary to permit rotation of dialyzer attachment member 120 with an attached dialyzer (not shown). Second outer coupling assembly 503 includes threaded insert 503a, wave springs 503b, spring spacer 503c, keyed washer 503d, washer 503e, and keyed washer 503f. Rotation member 130 can include one or more limit mechanisms (protrusion 130a) to limit the available angular rotation of dialyzer support member 120 and second outer coupling assembly 503 can include tension or resistance mechanism (503a, 503b, 503c, 503d, 503e, and 503f) to enable dialyzer holder 100 to securely hold a dialyzer (not shown) attached to dialyzer attachment member 120 at arbitrary angles. Second inner coupling assembly 504 is configured to fit inside second outer coupling assembly 503 and secure the dialyzer attachment member 120 to rotation member 130 along second axis of rotation 131. Second inner coupling assembly 504 can include a screw and corresponding washers to fasten dialyzer attachment member 120 to a corresponding screw hole in second male rotation interface 134 of rotation member 130.

Figure 6A:
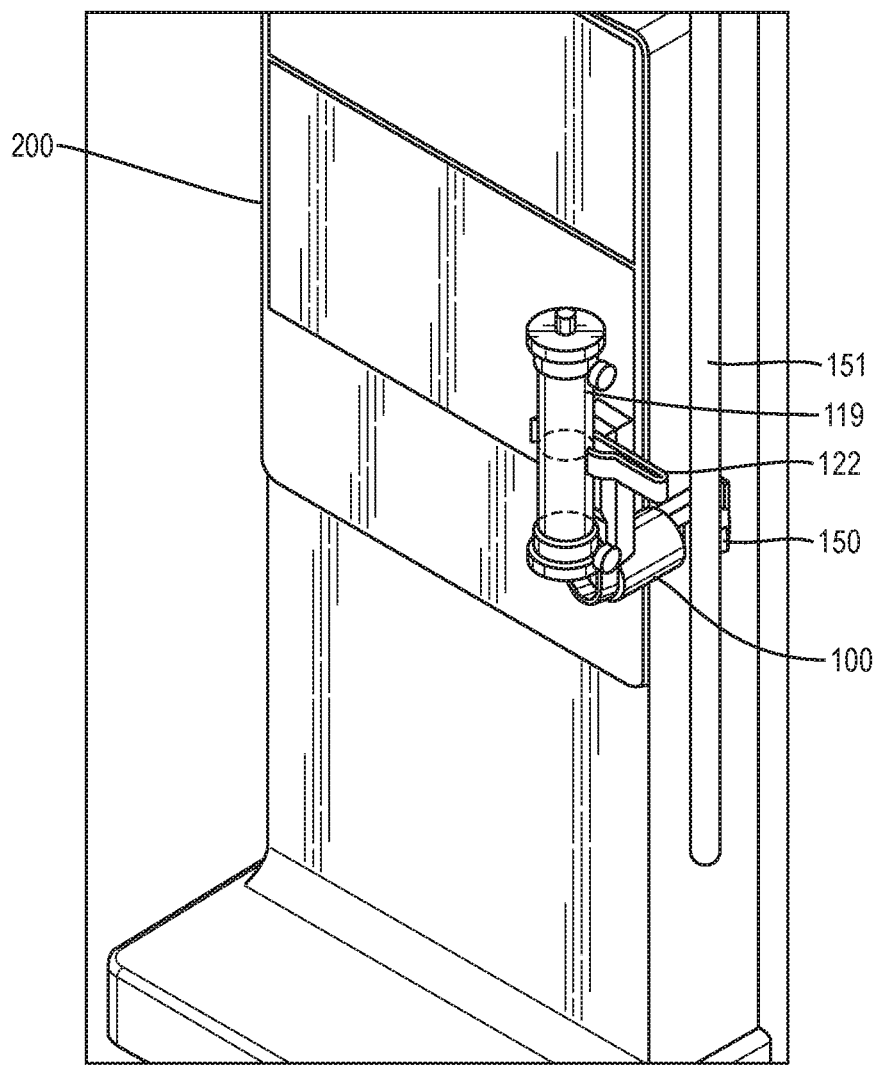
FIGS. 6A-C are diagrams of the operation of the dual-axis dialyzer holder of FIG. 3 with an attached dialyzer.
Figure 6B:
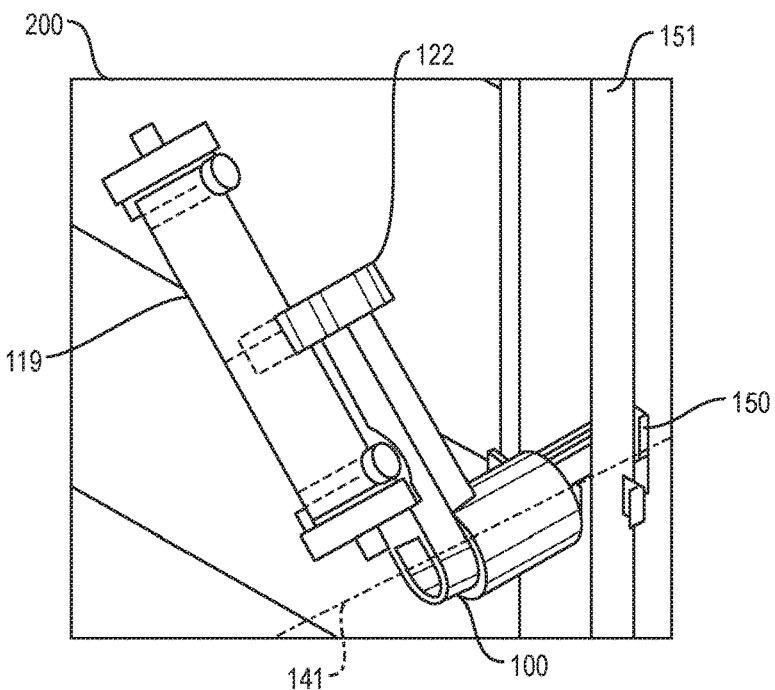
Figure 6C:
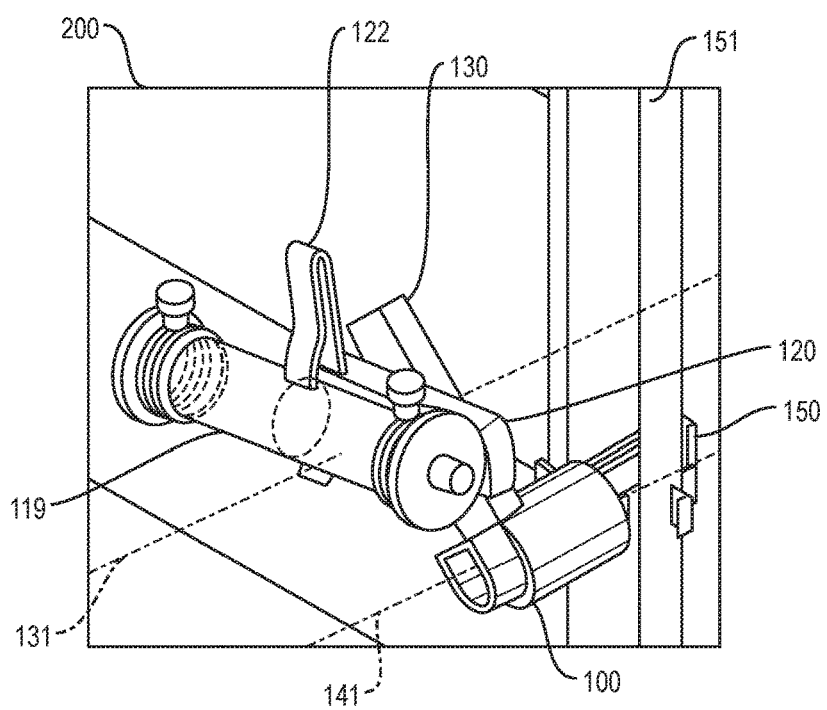

FIGS. 6A-C are diagrams of the operation of the dual-axis dialyzer holder 100 of FIG. 3 with an attached dialyzer 119. In FIG. 6A, a dual-axis dialyzer holder 100 having embodiments of the present invention is shown attached to support pole 151 of dialysis machine stand 200 by way of support clip 150. Flex clip 122 on dual-axis dialyzer holder 100 grasps dialyzer 119 and secures it to dual-axis dialyzer holder 100. Dialyzer 119 is shown in an upright (e.g., vertical or substantially vertical) position. In FIG. 6B dual-axis dialyzer holder 100, affixed to support pole 151, holds dialyzer 119 with flex clip 122 in a position rotated 45 degrees about first axis 141. FIG. 6C shows dialyzer 119 further rotated to prime the dialysate side of dialyzer 119. As an example, dialyzer attachment member 120 and rotation member 130 can be rotated can be rotated about 45 degrees from vertical about first axis 141 and dialyzer attachment member 120 can be rotated about 55 degrees from the first axis 141 rotation position about second axis 131, but other combinations are possible. In FIG. 6C the dialyzer 119 is rotated to a position 105 degrees from the position shown in FIG. 6A by way of a 55 degrees rotation of the dialyzer attachment member 120 with respect to the rotation member 130 about second axis 131. The resulting position of the dialyzer is sufficient for priming the dialysate side of the dialyzer, as similarly seen in FIG. 2. Compared to the single axis solutions, the present dual-axis design permits priming a dialyzer closer to the dialysis machine stand 200 with less horizontal translation, resulting in shorter overall tubing length. In addition, because of the close proximity between the dialyzer 119 and the dialysis machine stand 200 enabled by the dual-axis dialyzer holder 100, in some embodiments, the venous chamber (not shown) remains attached to the dialysis machine 199 during priming of the dialyzer 119.

Figure 7A:
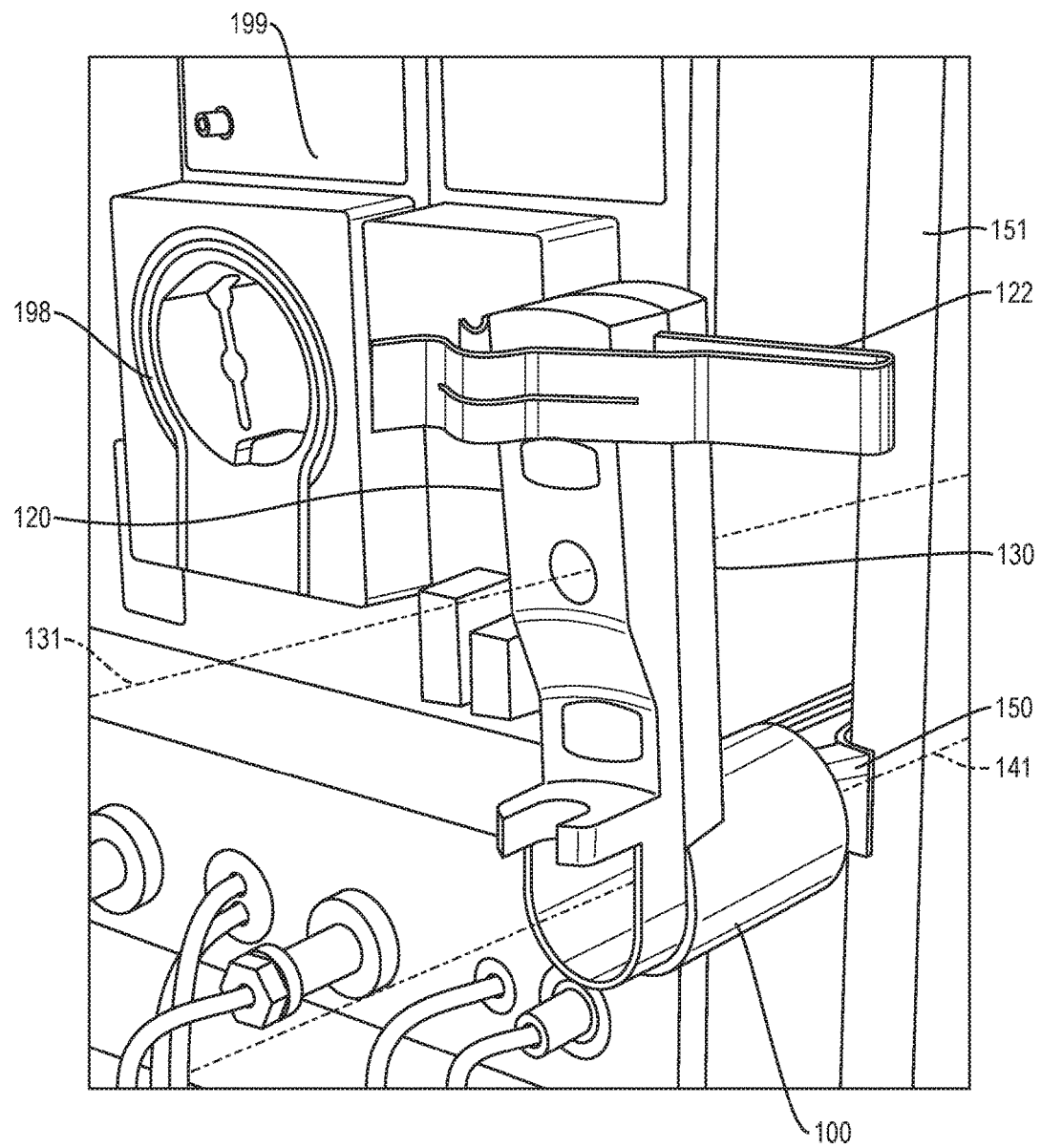
FIGS. 7A-C are photographs of the operation of the dual-axis dialyzer holder of FIG. 3 with an attached dialyzer connected to a dialysis machine.
Figure 7B:
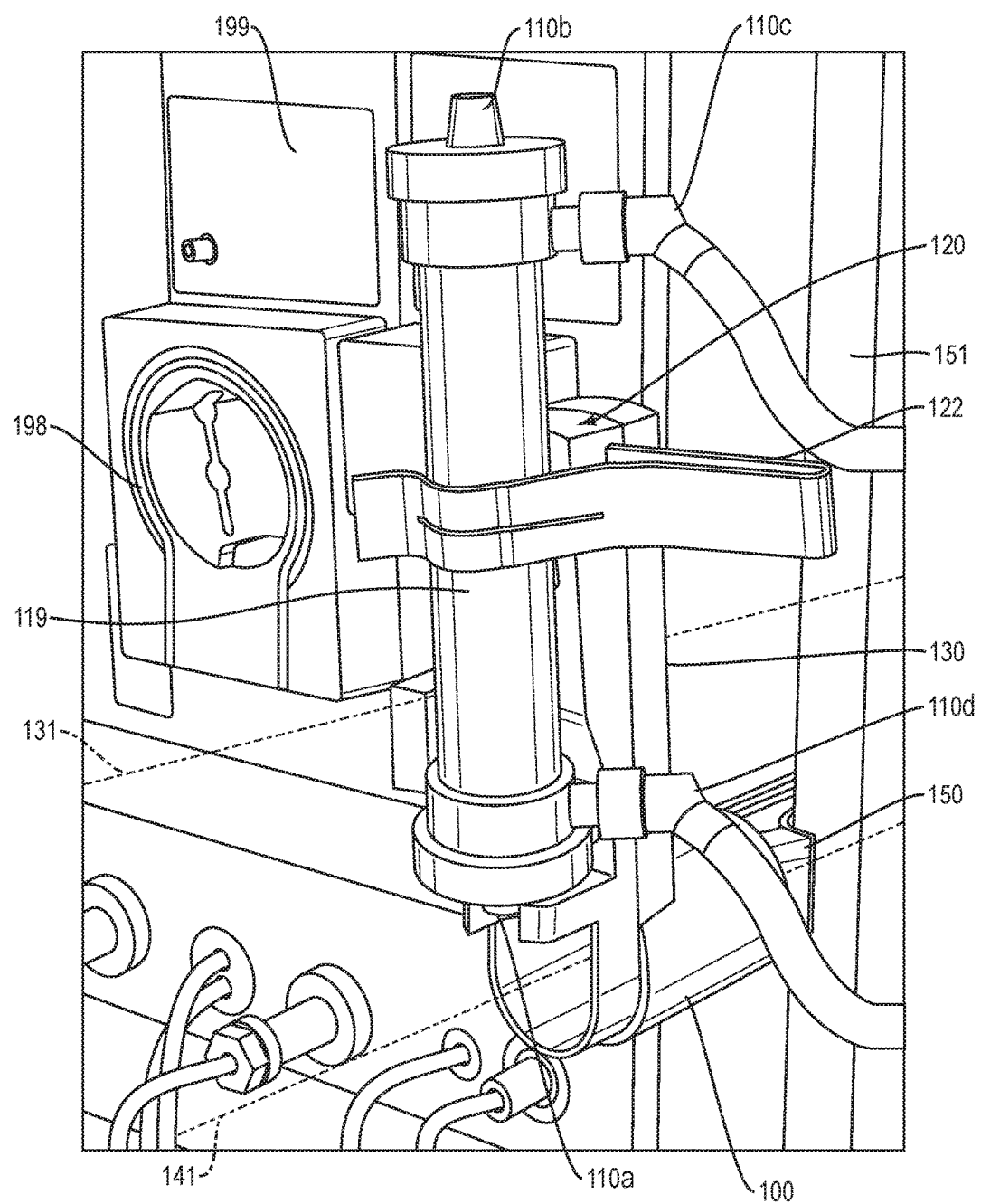
Figure 7C:
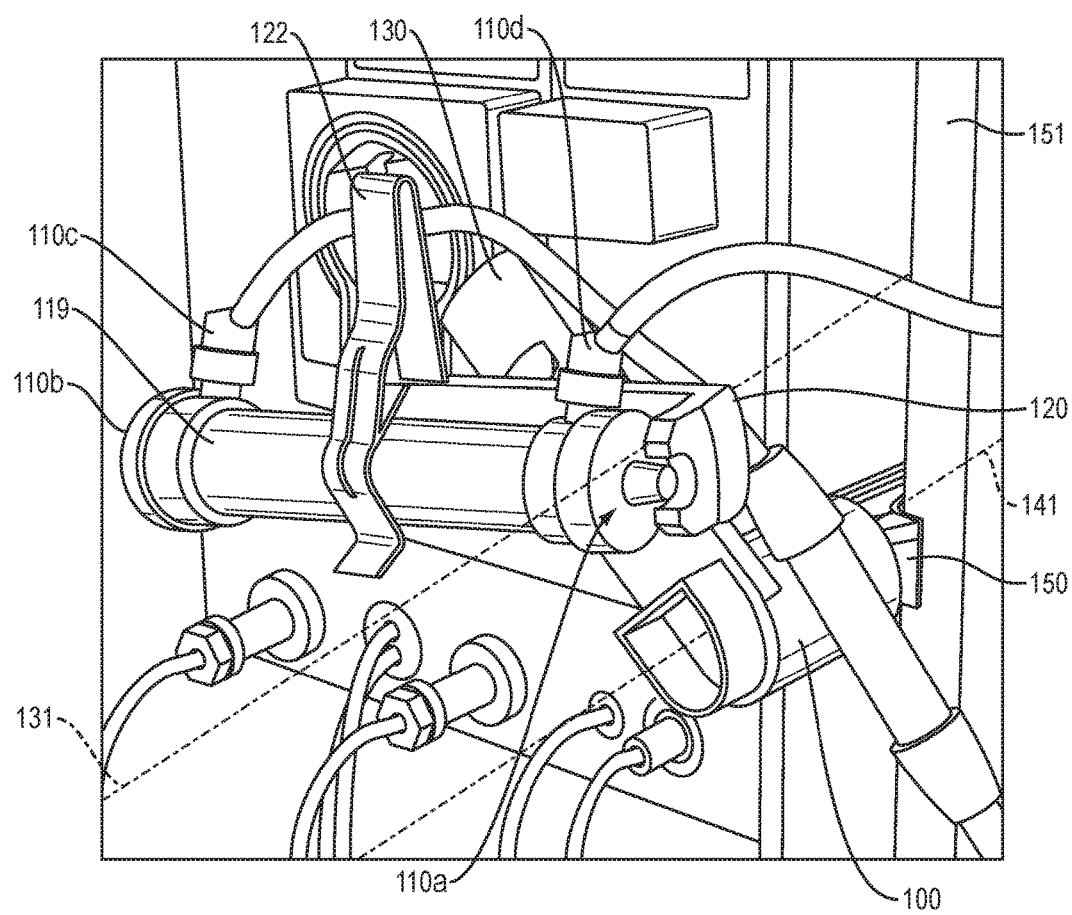

FIGS. 7A-C are photographs of the operation of the dual-axis dialyzer holder 100 of FIG. 6 with an attached dialyzer 119 connected to a dialysis machine 199. In FIG. 7A a dialyzer holder 100 is attached to support pole 151 by support attachment clip 150. In FIG. 7B a dialyzer 119 is attached to the dual-axis dialyzer holder 100 of FIG. 7A by a flex clip 122. The dialyzer 119 has a blood inlet port 110a and a blood outlet port 110b and a dialysate inlet port 110c and a dialysate outlet port 110d.

FIG. 7C shows the dialyzer 119 rotated about axes 131 and 141 of the dual-axis dialyzer holder 119 to position the dialysate outlet port 110d above the dialysate inlet port 110c, in order to remove air from the dialysate side of the dialyzer 119 and prime the dialysate side of dialyzer 119. The rotation member 130 of the dialyzer holder 100 is rotated about 45 degrees with respect to the dialyzer support member 140 about the first axis 141 and the support pole 151 and the dialyzer attachment member 120 is rotated about 55 degrees with respect to the rotation member 130 about the second axis 131.

An example embodiment of the present invention relates to a method of priming a dialysis machine 199. The method includes first, connecting a blood line (111a-c of FIG. 1) to a blood side of dialyzer 119, a dialysate line (not shown) to a dialysate side of dialyzer 119 as shown in FIG. 7A. A peristaltic pump 198 on the blood line configured to pump blood through the blood side of the dialyzer pump loop, pumps a volume of saline through the blood line, thereby priming the blood line. Second, rotating the dialyzer 119 from an upright (e.g., vertical or substantially vertical) position for priming of the blood side of the dialyzer to a position more than 90° from the substantially vertical position for priming of the dialysate side of the dialyzer, as shown in FIG. 7C, thereby allowing priming of the dialysate side of the dialyzer without disconnecting the blood side. Finally, pumping a volume of saline through the dialysate side of the dialyzer 119 in the rotated position to evacuate air from the dialysate side, and returning the dialyzer to a substantially vertical position as shown in FIG. 7B to begin a dialysis treatment.

While this invention has been particularly shown and described with references to example embodiments thereof, it will be understood by those skilled in the art that various changes in form and details may be made therein without departing from the scope of the invention encompassed by the appended claims.

What is claimed is:

1. A holder for a dialyzer having a blood side and a dialysate side both connected with tubing to a dialysis machine, the dialyzer having a length, said holder configured to allow priming of the blood side and the dialysate side of the dialyzer without disconnecting the blood side or dialysate side tubing from the dialysis machine, the holder comprising:

a dialyzer attachment member;
a first rotational assembly connected to the dialyzer attachment member and configured to allow the dialyzer to rotate from an upright position about a rotational axis perpendicular to the length of the dialyzer, the first rotational assembly comprising one or more limit mechanisms to limit angular rotation;
a second rotational assembly connected to the dialyzer attachment member and configured to allow the dialyzer to rotate about a second rotational axis perpendicular to the length of the dialyzer, the second rotational assembly comprising one or more limit mechanisms to limit angular rotation; and
a dialysis machine attachment member connected to the first rotational assembly, the dialysis machine attachment member securing the holder to the dialysis machine;
wherein the dialyzer can be rotated without disconnecting the blood side thereby allowing priming of the dialysate side of the dialyzer without disconnecting the blood side or dialysate side tubing from the dialysis machine.

2. The holder of claim 1, further including a venous chamber holder connected to the dialyzer attachment member, said venous chamber holder configured to attach a venous chamber the dialyzer, the venous chamber being fluidly connected to the blood side of the dialyzer.

3. The holder of claim 2, wherein the venous chamber includes an administration line having a hydrophobic vent adapted to remove gas from the dialyzer blood side.

4. The holder of claim 1, wherein the dialyzer can be rotated up to about 100° from vertical.

5. The holder of claim 1 wherein the first rotational assembly is further configured to rotate the dialyzer counterclockwise when facing the dialysis machine.

6. The holder of claim 1, wherein the second rotational assembly is further configured to rotate the dialyzer counterclockwise when facing the dialysis machine.

7. The holder of claim 1, wherein the first rotational assembly allows the dialyzer to rotate to a position about 45° from the upright position.

8. The holder of claim 1, wherein the second rotation assembly allows the dialyzer to rotate to a position about 55° from the upright position.

9. The holder of claim 1, wherein the first rotational assembly comprises a tension or resistance mechanism so that the holder securely holds a dialyzer attached to dialyzer attachment member at arbitrary angles.

10. The holder of claim 1, wherein the second rotational assembly comprises a tension or resistance mechanism so that the holder securely holds a dialyzer attached to dialyzer attachment member at arbitrary angles.

* * * * *